United States Patent [19]
Saunders et al.

[11] Patent Number: 5,503,633
[45] Date of Patent: Apr. 2, 1996

[54] OSTOMY BAG CLEANING APPARATUS

[75] Inventors: Philip K. Saunders, Manteo, N.C.; Lawrence F. Shaffer, III, New Freedom, Pa.; Lawrence F. Shaffer, IV, Kill Devil Hills; Burwell R. Evans, Manteo, both of N.C.; Michael W. Millard, Baldwin, Md.

[73] Assignee: Butler & Hanby, Inc., Parkton, Md.

[21] Appl. No.: 291,191

[22] Filed: Aug. 16, 1994

[51] Int. Cl.$^6$ ....................................................... A61F 5/44
[52] U.S. Cl. ............................ 604/332; 604/334; 4/661; 4/340
[58] Field of Search ..................................... 604/332–338, 604/277; 4/661, 340–342

[56] References Cited

U.S. PATENT DOCUMENTS

| | | | |
|---|---|---|---|
| 2,438,073 | 3/1948 | Saur | 604/277 |
| 2,584,249 | 2/1952 | Belcher . | |
| 2,689,567 | 9/1954 | Welch . | |
| 2,869,547 | 1/1959 | Yohe | 604/334 |
| 3,500,480 | 3/1970 | Michal, Jr. | 4/341 |
| 4,050,461 | 9/1977 | Ruby . | |
| 4,134,404 | 1/1979 | Williams, Jr. | 604/277 |
| 4,654,037 | 3/1987 | Fenton | 604/334 |
| 4,755,177 | 7/1988 | Hill | 604/336 |
| 4,766,622 | 8/1988 | Pacelli | 604/277 |
| 4,995,410 | 2/1991 | Lash . | |

OTHER PUBLICATIONS

Commercial Brochure for Ostomy Bag Flush, Irrigation Devices, Inc., Lorain, Ohio Found by Applicant approximately Apr., 1994.

Primary Examiner—Randall L. Green
Assistant Examiner—Mark O. Polutta
Attorney, Agent, or Firm—Olive & Olive

[57] ABSTRACT

The present invention comprises a novel apparatus for the cleaning of an ostomy bag being worn by an ostomy patient. The cleaning apparatus of the invention is configured in three embodiments capable of fixed installation, portable use and bedside use, respectively. The apparatus of the fixed and portable embodiments provides a support for a patient at a sufficient height above a toilet bowl in the form of a platform having support bars with security stops and a chute removably hung from said platform to discharge excreta into the bowl. The fixed embodiment employs a hose for attachment to house water supply and a nozzle adapted to clean within the ostomy bag. The portable embodiment employs a reservoir which supplies pressurized water either by elevation or by use of a portable pump. The convalescent embodiment is adapted to be used at the bedside and has a fluid reservoir/ portable pump, hose and a collecting tank, such as a bedpan mounted to receive the excreta being cleaned from the ostomy bag.

12 Claims, 4 Drawing Sheets

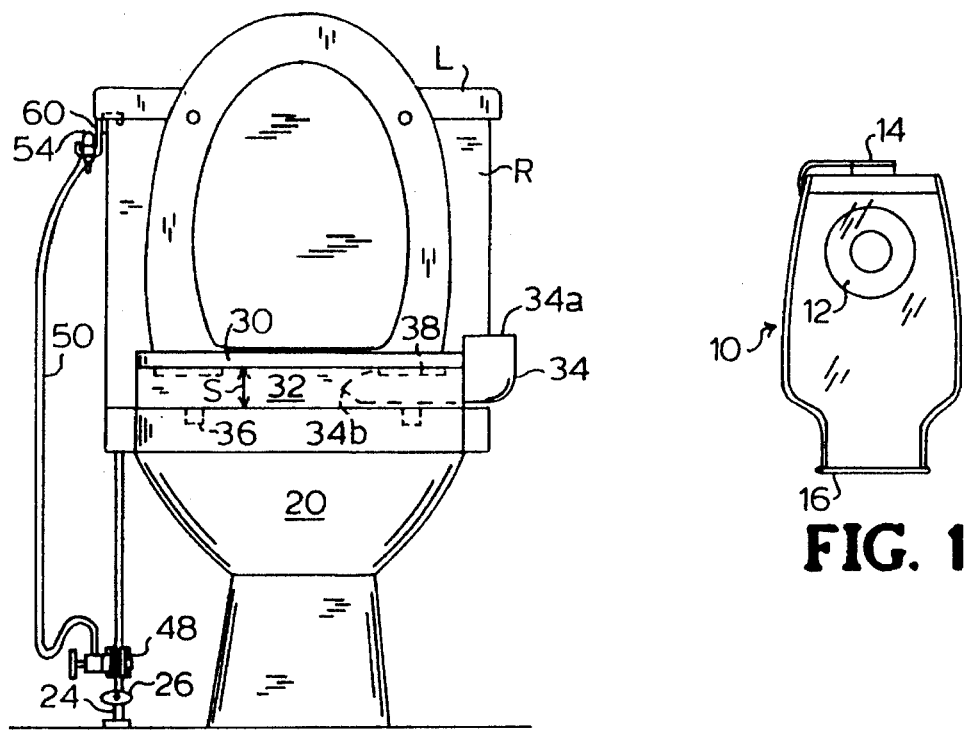
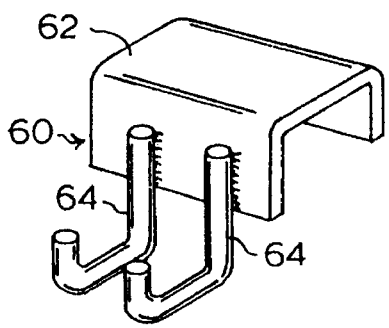
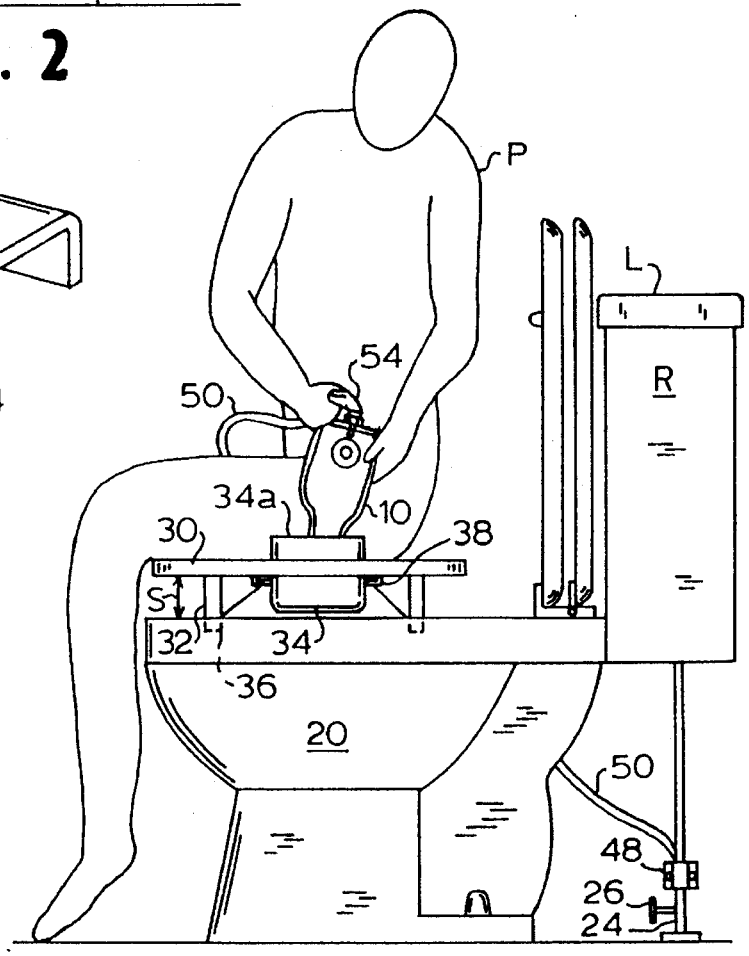

OSTOMY BAG CLEANING APPARATUS

FIELD OF THE INVENTION

This invention relates to the field of post-surgical apparatus, and more particularly to apparatus for the cleaning of ostomy bags.

BACKGROUND OF THE INVENTION

Subsequent to an ostomy operation in which portions of the intestinal or urinary tract are removed, the waste products produced by the body are excreted at the residual opening, or stoma, formed in the abdominal wall. The excreta is typically collected by attaching an ostomy bag having an adhesive coated ring to the outer side of the stoma. When full, which may happen several times in a day, this ostomy bag must be either removed and discarded, or cleaned. There are two principal reasons to avoid the removal and discarding of the filled ostomy bag. The first reason is that removal and replacement is irritating to the skin of the patient, and therefore should be done as infrequently as possible. Second is that discarding human waste into a garbage disposal facility, even if it is contained in a plastic bag, may cause the spread of disease. Alternatively, cleaning the bag contents into a facility adapted for handling sewage is substantially safer.

Therefore, the preferred method is to leave the ostomy bag in place and to clean or flush the excreta into a toilet where such materials are able to be disposed of sanitarily.

Additional problems in the cleaning and care of an ostomy bag will occur if the patient involved is restricted to bed or to a wheelchair because of the severity of illness. A different sort of problem is presented if the ostomy patient is otherwise healthy and able to travel, so that the ostomy bag cleaning sometimes occurs in a location other than home.

It is therefore an object of this invention to provide a bag adapted to be worn in contact with a patient's abdomen adjacent a stoma site and operational for collecting excreta and an apparatus adapted for cleaning the collection bag without removal of the bag from the patient's abdomen.

It is a further object of this invention to provide an apparatus for the cleaning of the ostomy bag and discharging the removed excreta into a sanitary sewage facility.

It is an additional object of this invention to provide an ostomy bag cleaning apparatus which can be brought to the side of a patient wearing the ostomy bag and confined to bed or a wheelchair and used to clean the ostomy bag at the bedside.

It is a still further object of this invention to provide an ostomy bag cleaning apparatus which can be readily transported and utilized in any toilet facility.

Other objects and advantages will be more fully apparent from the following disclosure and appended claims.

SUMMARY OF THE INVENTION

The present invention provides an apparatus adapted to wash the interior of an ostomy bag while it is being worn by the patient and to discharge the effluent into a toilet bowl. The apparatus is configured in three embodiments respectively capable of fixed installation, bedside use and portable use. The ostomy bag cleaning apparatus comprises a source of water under pressure, a connective flexible hose with a valve-controlled wash nozzle, a seating platform which mounts on a toilet bowl and a discharge chute which removably attaches to the platform with an entry end exposed adjacent the ostomy bag and an exit end adjacent the toilet bowl. In the embodiment intended for bedside use, the apparatus has a reservoir of cleaning fluid, a pump and an excreta receiving tank.

BRIEF DESCRIPTION OF THE DRAWINGS

FIG. 1 is an elevation view of an ostomy bag that is usable as part of the bag cleaning apparatus of the invention.

FIG. 2 is a front elevation view of a fixed location ostomy bag cleaning apparatus of the invention mounted on a toilet.

FIG. 3 is a side elevation view of the cleaning apparatus of FIG. 2 with a patient positioned to clean an ostomy bag without removal from its stomal attachment.

FIG. 4 is a perspective view of a rack for temporarily supporting a hose nozzle of the invention cleaning apparatus.

DETAILED DESCRIPTION OF THE INVENTION

Figure 5:
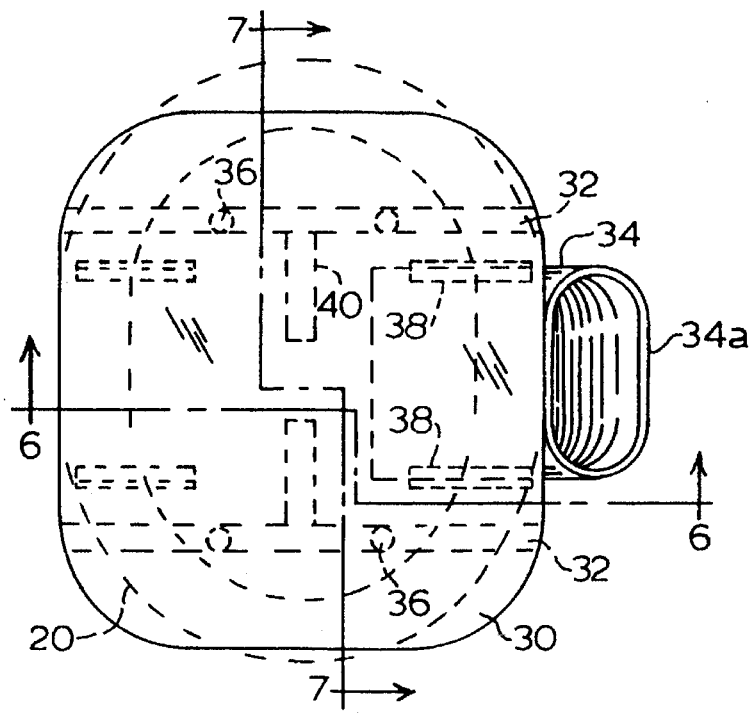
FIG. 5 is a top plan view of a patient seating platform with a discharge chute of the invention.

According to the location and type of intestinal malfunction, a stoma may be formed on either the right or the left abdominal wall, slightly below the patient's waist. Therefore, for correct cleaning of an ostomy bag without removal from the patient, a cleaning apparatus must be able to reach either the left or right side of the patient. However, the water connections for standard toilets in this country are fixed in position, generally at the left side of the toilet, when viewed from in front of the toilet. Thus any permanently installed ostomy bag cleaning apparatus must be adaptable to cross to the left side of the patient in a case of a left stoma.

Such an installation of a fixed location ostomy bag cleaning apparatus usable at either a left or right stoma site is illustrated in FIGS. 2 and 3. As seen in front view in FIG. 2, seating platform 30 is supported above toilet bowl 20 by a pair of support bars 32 or other means able to support platform 30 over toilet bowl 20 as contemplated by the invention. A space S is maintained between the upper lip of toilet bowl 20 and the bottom surface of seating platform 30 so that curved discharge chute 34 passes therebetween. As seen in detail in FIGS. 5, 6 and 7, discharge chute 34 is held securely to the lower surface at a side edge of seating platform 30 by chute slides 38.

Figure 8:
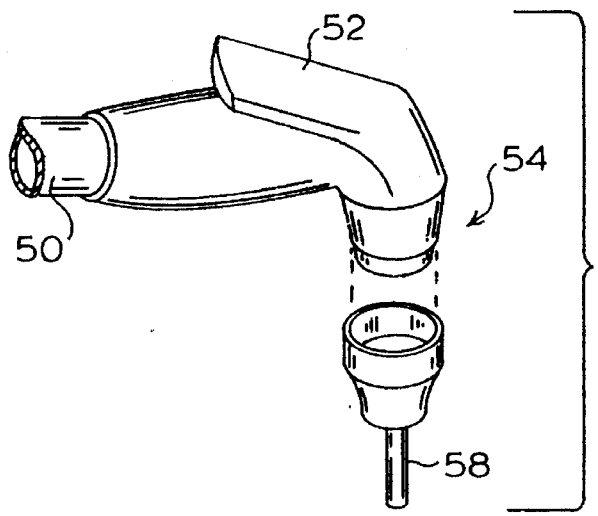
FIG. 8 is a perspective view of a hose valve and nozzle of the invention.

Water is connected to the apparatus of the invention from conventional house water supply piping 24, and preferably downstream of house water valve 26 (FIGS. 2 and 3). Water supply connection 48, of any known type, is connected to a supply end of bag wash hose 50. In the preferred embodiment, connection 48 comprises a saddle valve. The discharge end of hose 50 is fitted with a hose nozzle 54, shown in detail in FIG. 8. A rack 60, discussed in detail in regard to FIG. 4, is provided to support nozzle 54 in a convenient position when nozzle 52 is not in use.

The cleaning apparatus of the invention may be used with conventional ostomy bags having only a lower opening, but is preferred to be used with an ostomy bag 10 of the type illustrated in FIG. 1. Ostomy bag 10 is formed of a liquid impermeable polymer and has three openings: a stoma mating adhesive coated ring 12 in one side panel; a relatively small top opening 14 in bag 10 which is maintained closed by a snap closure as is well known; and bottom opening 16 formed in the bottom end of bag 10 and adapted to release collected excreta from bag 10 during cleaning and be subsequently reclosed securely.

The rack 60, adapted to support hose nozzle 52 is illustrated in FIG. 4. Rack 60 includes downwardly curved clip 62 which is formed of thin sheet material in a shape to engage the upper lip of a conventional toilet bowl reservoir R without significantly interfering with the normal positioning of its lid L. Rack 60 is formed with upwardly curved hooks 64 which are positioned and shaped to support nozzle 54. Rack 60 may be fabricated of multiple metal parts affixed by welding or other known means to one another as shown. Alternately, rack 60 may be formed of a single molded plastic piece, in which case the junction between hooks 64 and clip 62 can be made smooth. The choice of material in this and other parts of the invention is an economic, aesthetic, and a functional decision.

FIG. 3 shows a side view of the apparatus of FIG. 2 with an ostomy patient P seated upon seating platform 30 and performing the operation of cleaning ostomy bag 10 of accumulated excreta. Patient P is holding nozzle 54 into the upper opening of ostomy bag 10, with the lower end of ostomy bag 10 being open and inserted into the entry 34a of discharge chute 34. As water flows from nozzle 52, the accumulated excreta is washed through chute 34 into the toilet bowl 20.

As shown in FIG. 3, patient P is seated on substantially flat seating platform 30 which is mounted, in turn, on toilet bowl 20 in spaced relation therefrom by support bars 32. As is shown, space S is of a size to permit chute 34 to be positioned between platform 30 and toilet bowl 20.

Figure 6:
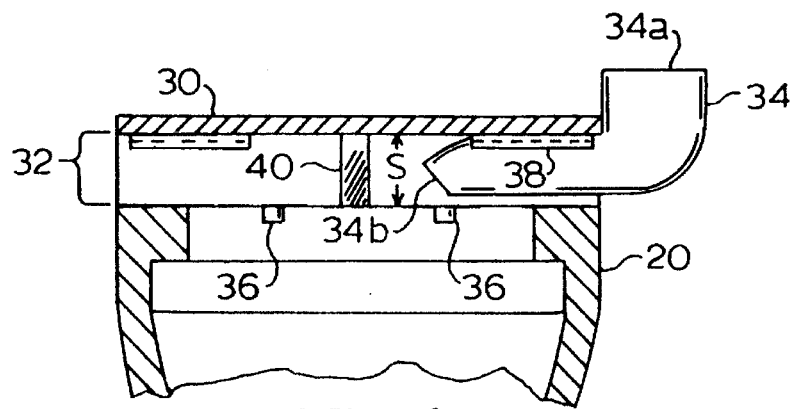
FIG. 6 is a cross sectional view of the patient seating platform taken in the direction of line 6—6 of FIG. 5.
Figure 7:
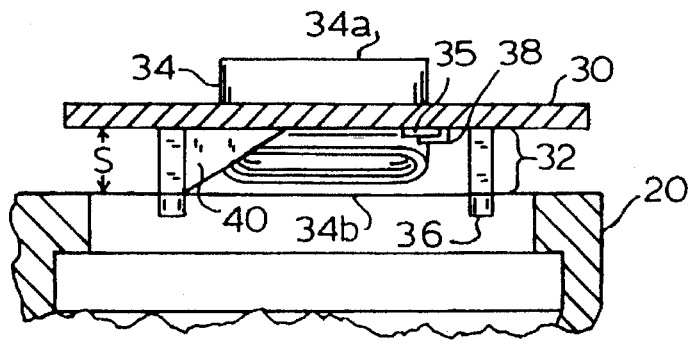
FIG. 7 is a cross sectional view of the patient seating platform taken in the direction of line 7—7 of FIG. 5.

Details of the structure of platform 30 and chute 34 are illustrated more fully in FIGS. 5, 6 and 7. Parallel support bars 32 are fixedly connected to the undersurface of platform 30 in positions to respectively span the rear and forward portions of the opening in toilet bowl 20. Each support bar 32 is stabilized in its normally perpendicular relation to platform 30 by a rigid brace 40 near the center of each bar 32. In the preferred embodiment, brace 40 is triangular in shape as illustrated in FIG. 7. A pair of stops 36 is provided on the lower surface of each support bar 32, each stop 36 being placed so as to enter the opening in toilet bowl 20 and prevent platform 30 from moving sufficiently to either side of its central position as to compromise the secure support of the patient. Support bars 32 and stops 36 are configured to accommodate substantially any current standard model of toilet bowl 20 and securely support seating platform 30 thereupon.

Discharge chute 34 is configured as an "L" shaped funnel. In the preferred embodiment, chute 34 is oval in cross section, although funnels of other shapes, e.g., round, would function adequately. Entry end 34a is somewhat larger in size than discharge end 34b. Discharge chute 34 is formed with a pair of laterally disposed external rails 35 which function to engage one of two available pairs of mating slide brackets 38a, 38b positioned on either side of the lower surface of platform 34. Chute 30 may be mounted on either the left or right side of platform 30. When chute 34 is mounted beneath and adjacent platform 30, its discharge end 34b, which is preferably curved downwardly, will cause the effluent excreta and water from bag 10 to empty into toilet bowl 20 without contacting any of the structure of platform 30. The entry end 34a of chute 34 is positioned higher than the upper surface of platform 30. Rails 35 engage slide brackets 38 so as to hold chute 34 in place and to allow chute 34 to be easily removed when necessary for transport or for cleaning.

It is to be noticed that since the function of the present invention deals with a removal of human waste material, minimization of accumulation and ease of cleaning parts are significant requirements. The components of the invention are preferred to be made either of stainless steel or molded plastic, such as high density polyethylene, with smoothly polished surfaces. The final choice between the preferred materials is determined by the expected service life, mode of cleaning and cost. For example, in a hospital or other clinical setting, a stainless steel unit may be preferred to extend its life and to allow possible cleaning with harsh chemical cleaners or in a mechanized cleaning process.

Returning to FIG. 3, patient P cleans ostomy bag 10 by first opening its bottom opening 16 and placing it into the entry end 34a of discharge chute 34, next opening the top bag opening 14 and placing the tip 58 of nozzle 54 (see FIG. 8) into top opening 14. Patient P controls water flow by pressing the handle of valve 52 mounted on nozzle 54 as tip 58 is moved about within bag 10 to clean all areas. The water and excreta are flushed through chute 34 into toilet 20. Even in the case of urinary waste which readily flows from bottom opening 16, flushing the interior of bag 10 is necessary for reasons of sanitation and odor control.

The above described embodiment of the invention relates to a permanently installed ostomy bagwash apparatus in a home bathroom. Since ostomy patients are of many differing states of health and activity, other embodiments, especially for use with a convalescent patient confined to bed or for use in travel with a patient who is otherwise healthy, are also useful. Thus, two additional embodiments, being variations of the first embodiment, are described below.

Figure 10:
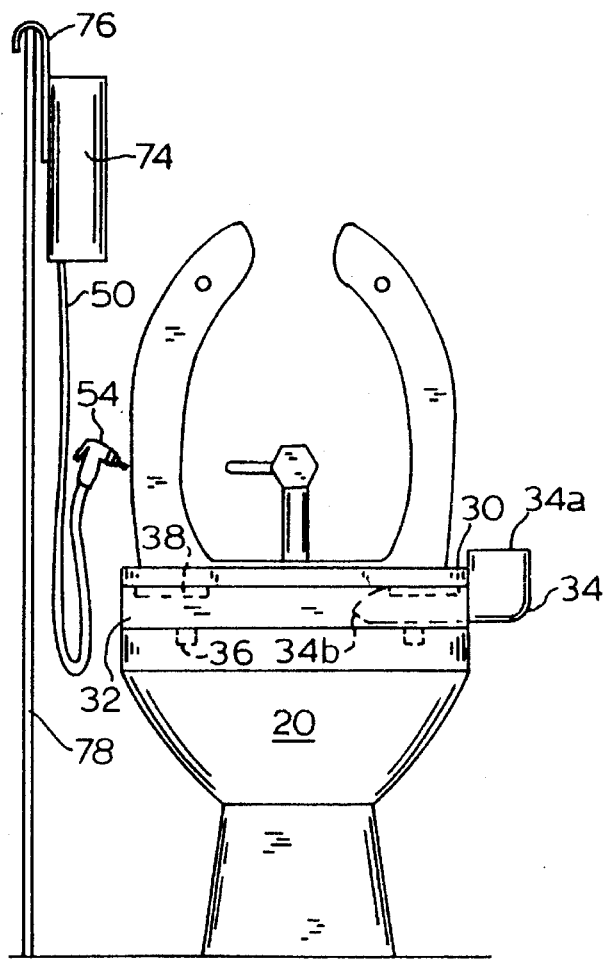
FIG. 10 is a front elevation view of a second embodiment of a portable ostomy bag cleaning apparatus according to the invention.
Figure 9:
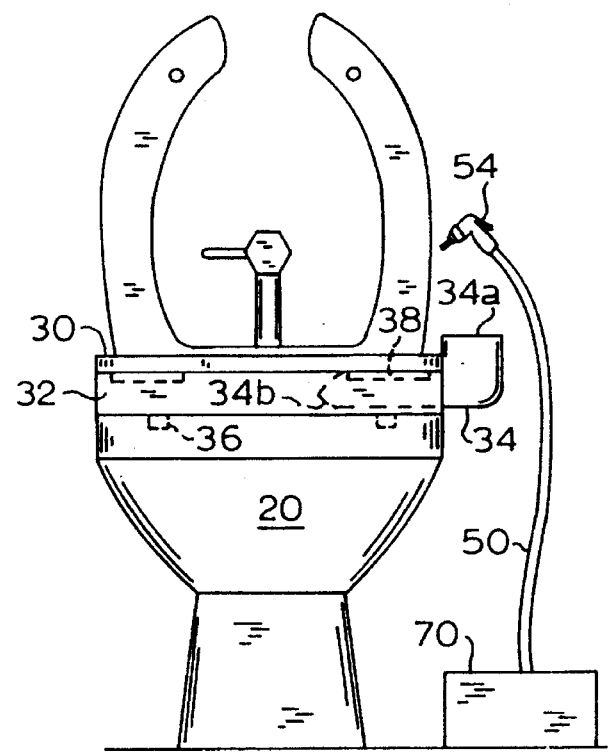
FIG. 9 is a front elevation view of a first embodiment of a portable ostomy bag cleaning apparatus of the invention mounted on a toilet.

FIGS. 9 and 10 show two modified versions of a portable second embodiment of the invention. In both versions shown in FIGS. 9, 10, the same platform 30, discharge chute 34 and related components are used as those described above. In the travel context, permanent connection to installed plumbing is not feasible. When using either portable system of FIG. 9 or 10, reservoir/pump 70 is filled with water or an other cleaning fluid before beginning the cleaning process at the toilet.

FIG. 9 shows an apparatus for washing ostomy bags according to the invention with a reservoir/pump 70 placed on the floor adjacent toilet bowl 20. The pump utilized may be either battery powered with a switch connected to nozzle 54, or a foot operated pump. Either type of pump is reasonably available from a variety of sources.

In the embodiment shown in FIG. 10, the filled water supply bottle 74 is held elevated above toilet bowl 20 by hook 76 which may be hung on separating wall 78 or other convenient support. Water flow is motivated by gravity when nozzle 54 is actuated. In other respects this embodiment functions as described above.

When transporting the apparatus of either portable model, discharge chute 34 is removed from platform 30 with support bars 32 remaining in place. Platform 30, chute 34, water reservoir/pump 70 (or water bottle 74) and hose 50 are carried in a "tote bag". Other supplies, such as spare ostomy bags, may also be carried in such a "tote bag". To use either portable model cleaning apparatus, the parts are taken out of the bag, chute 34 is slid into chute slides 38 beneath platform 30, platform 30 is placed on toilet bowl 20 and the water container is filled. Since weight is a factor in a portable apparatus, the components of either of these embodiments are preferred to be of molded plastic.

Figure 13:
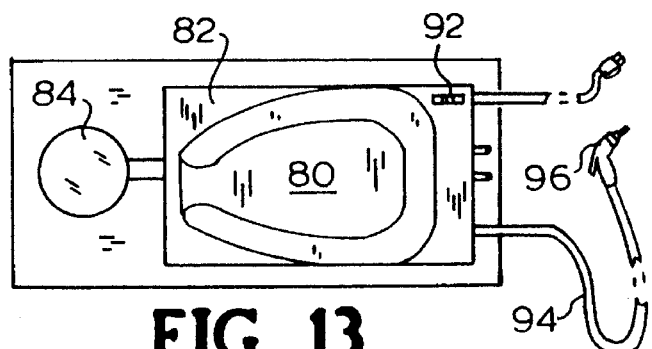
FIG. 13 is a top plan view of the apparatus of FIG. 12.
Figure 12:
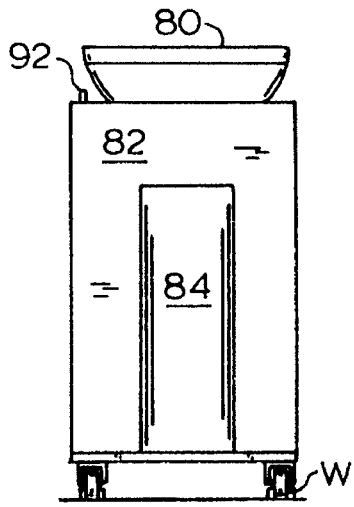
FIG. 12 is a front elevation view of the apparatus of FIG. 11.
Figure 11:
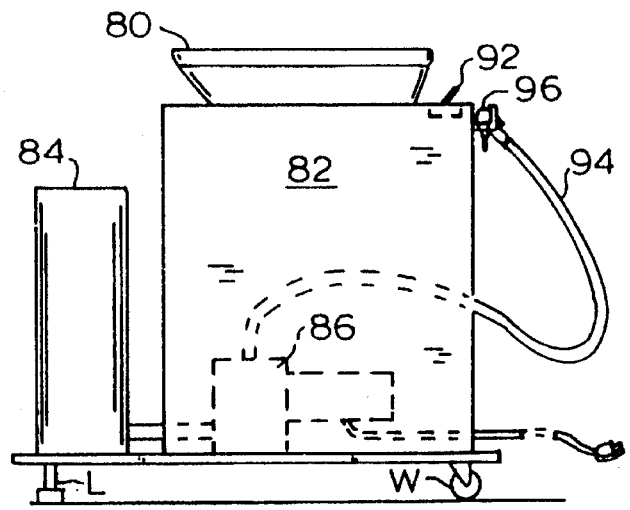
FIG. 11 is a side elevation view of a ostomy bag cleaning apparatus adapted for bedside use.

In the third embodiment, which is adapted for use with a patient confined to a chair or bed, it is necessary to provide a receptacle for removed excreta and water beside the patient's bed. Since this third embodiment is intended for use with a confined patient, no seating platform is provided. As illustrated in FIGS. 11, 12, 13 receptacle 80 is removably supported on a housing 82 which contains a pump. Housing 82 is configured with its top somewhat lower than the height of a typical wheelchair or bed. Pump 82 is fixedly connected to reservoir 84 for a supply of water, or other cleaning fluid, and has a discharge hose 94 with nozzle 96 on its discharge end. Once connected to a source of power, pump 86 is activated by switch 92. Receptacle 80, typically a bedpan in a hospital setting, is removed when full for cleaning into a toilet. The confined patient ostomy bag cleaning apparatus is preferably mounted on a pair of wheels W at a first end and a pair of legs L at a second end for easy transport and for stable positioning when in use.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

We claim:

1. An apparatus for the collection and disposal of bodily excreta by an ostomy patient, comprising:
   (a) a substantially planar seating platform having a lower surface and adapted to be positioned during use of said apparatus a selected distance above and parallel to the upper lip Of a toilet bowl on support bars attached to and extending across said lower surface and adapted to support said ostomy patient upon said seating platform;
   (b) each said support bar formed with one or more stops extending perpendicularly in a direction away from said seating platform and configured to extend adjacent said upper lip to prevent said seating platform from lateral movement relative to said toilet bowl;
   (c) a chute removeably attached to said lower surface so as to pass between said platform and said toilet bowl and having a first end for receiving excreta being disposed of and a second end for discharging excreta into said toilet bowl;
   (d) controllable supply means adjacent said toilet bowl for providing fluid to aid in the disposal of said excreta; and
   (e) wherein said apparatus is operative for disposal of excreta when said patient is seated on said seating platform.

2. The apparatus as claimed in claim 1, wherein said chute comprises a tubular member configured to be positioned between said platform and said toilet bowl.

3. The apparatus as claimed in claim 2, wherein said chute further comprises means adapted to removably secure said chute to said lower surface of said platform.

4. The apparatus as claimed in claim 1, further comprising an ostomy bag having a closeable bottom opening adapted for emptying the contents of said bag and a closeable top opening adapted to receive said fluid so as to clean said excreta from said ostomy bag when said bottom and top openings are open.

5. The apparatus as claimed in claim 1, wherein said supply means comprises a flexible hose connected at its inlet end to a source of pressurized cleaning fluid and having a valve and nozzle connected at its discharge end.

6. The apparatus as claimed in claim 4, wherein said supply means comprises a flexible hose connected at its inlet end to a source of pressurized cleaning fluid and having a valve and nozzle connected at its discharge end.

7. The apparatus as claimed in claim 6, wherein said nozzle is adapted to be inserted into said ostomy bag.

8. The apparatus claimed in claim 5 wherein said source of pressurized water comprises a connection to a fixed water supply pipe of a building in which said apparatus is installed and said cleaning fluid comprises water.

9. The apparatus as claimed in claim 7 wherein said source of pressurized water comprises a fluid reservoir adapted to be positioned at an elevated distance above the height of said platform.

10. The apparatus claimed in claim 7 wherein said source of pressurized water comprises a fluid reservoir and a portable pump.

11. The apparatus claimed in claim 5, further comprising a rack adapted to be removably hung in the vicinity of said patient and able to support said hose nozzle.

12. An apparatus for the collection and disposal of bodily waste products discharged from a stoma, comprising:
   (a) an ostomy bag having a closeable bottom opening adapted for emptying the contents of said bag and a closeable top opening adapted to receive a cleaning fluid from a nozzle so as to clean said waste products from said ostomy bag when said bottom and top opening are open;
   (b) a substantially planar seating platform having a lower surface and adapted to be removably position a selected distance above and parallel to the upper lid of a toilet bowl on support bars attached to and extending across said lower surface and adapted to support an ostomy patient upon said seating platform;
   (c) each said support bar formed with one or more stops extending perpendicularly in a direction away from said seating platform and configured to extend adjacent said upper lip to prevent said seating platform from lateral movement relative to said toilet bowl;
   (d) a chute removably attached to said lower surface so as to pass between said platform and said toilet bowl and having a first end for receiving excreta being disposed of and a second end for discharging excreta into said toilet bowl; and
   (e) a flexible hose connected at an inlet end to a source of cleaning fluid and a valve having a nozzle adapted to engage said ostomy bag top opening;
   (f) wherein said apparatus is operative for disposal of excreta when said patient is seated on said seating platform.

* * * * *